(12) United States Patent
Bujard

(10) Patent No.: US 7,223,472 B2
(45) Date of Patent: May 29, 2007

(54) GLOSS PIGMENTS HAVING HIGH COLOUR SATURATION

(75) Inventor: Patrice Bujard, Reinach (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/504,413

(22) PCT Filed: Mar. 4, 2003

(86) PCT No.: PCT/EP03/02196

§ 371 (c)(1),
(2), (4) Date: Aug. 9, 2004

(87) PCT Pub. No.: WO03/076520

PCT Pub. Date: Sep. 18, 2003

(65) Prior Publication Data

US 2005/0090583 A1 Apr. 28, 2005

(30) Foreign Application Priority Data

Mar. 11, 2002 (CH) .................................. 418/02
Jul. 30, 2002 (CH) ................................. 1334/02

(51) Int. Cl.
*B32B 5/66* (2006.01)
(52) U.S. Cl. ..................... 428/403; 428/404; 428/405; 428/406; 428/407; 106/404; 523/440
(58) Field of Classification Search ................ 428/403, 428/404, 405, 406, 407; 106/404; 523/440
See application file for complete search history.

(56) References Cited

U.S. PATENT DOCUMENTS

| 5,472,491 A | 12/1995 | Duschek et al. ............ 106/418 |
| 5,766,335 A * | 6/1998 | Bujard et al. ............... 106/404 |
| 5,855,660 A * | 1/1999 | Bujard et al. ............... 106/418 |
| 6,270,840 B1 | 8/2001 | Weinert ....................... 427/251 |
| 6,689,205 B1 | 2/2004 | Brückner et al. ........... 106/415 |
| 2003/0075079 A1 | 4/2003 | Sommer ...................... 106/442 |

FOREIGN PATENT DOCUMENTS

| CA | 2366953 | 10/2000 |
| DE | 19618569 | 11/1997 |
| EP | 0874026 | 10/1998 |
| WO | 01/25500 | 4/2001 |

OTHER PUBLICATIONS

Ciba Specialty Chemicals Corp. Application No. 10/870,643 filed Jun. 10, 2004.
Ciba Specialty Chemicals Corp. Application No. 10/870,644 filed Jun. 10, 2004.

* cited by examiner

*Primary Examiner*—Leszek Kiliman
(74) *Attorney, Agent, or Firm*—Joseph C. Suhadolnik

(57) ABSTRACT

The invention relates to coloured gloss pigments having specific particle dimensions comprising a transparent core of a silicon oxide of the composition $SiO_{0.03}$ to $SiO_{0.95}$ and, optionally, further coatings of silicon dioxide, carbon, a partially transparent metal and/or a dielectric of high refractive index, to a coating method suitable therefor wherein metallic silicon is vapour-deposited in the presence of a low oxygen partial pressure, to the use of such gloss pigments in pigmenting plastics, surface coatings, printing inks and cosmetic compositions, and also to pigmented compositions comprising such gloss pigments.

10 Claims, 2 Drawing Sheets

GLOSS PIGMENTS HAVING HIGH COLOUR SATURATION

Figure 1:
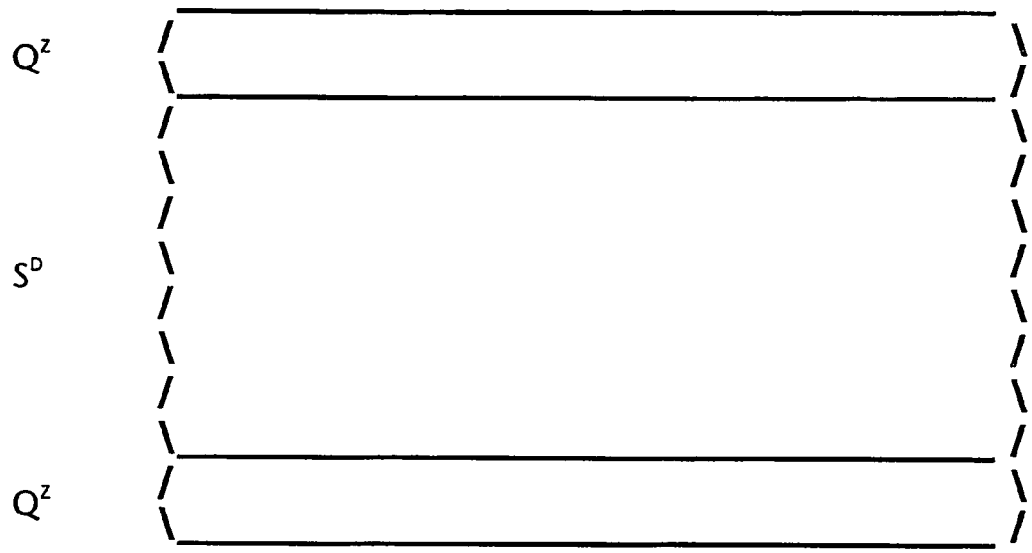

The invention relates to coloured gloss pigments having specific particle dimensions, comprising a transparent core of a silicon oxide of composition $SiO_{0.03}$ to $SiO_{0.95}$ and, optionally, further coatings of silicon dioxide, carbon, a partially transparent metal and/or a dielectric of high refractive index, to a coating method suitable therefor wherein metallic silicon is vapour-deposited in the presence of a low oxygen partial pressure, to the use of such gloss pigments in pigmenting plastics, surface coatings, printing inks and cosmetic compositions, and also to pigmented compositions comprising such gloss pigments.

The invention belongs to the field of effect pigments, that is to say reflecting flat particles whose radiation reflection is of different brightness and/or has a different reflection spectrum depending on the angle to the flat surface. In a surface coated using effect pigments, for example, the effect pigment particles tend to be oriented, within the surface coating, substantially parallel to the surface so that the coloured surface of the coating, when illuminated from a fixed white light source, is capable of exhibiting different colours depending on the viewing angle and the nature of the effect pigment. Effect pigments which are, for example, incorporated into a surface coating layer applied to vehicle bodywork accordingly give the vehicle an attractive appearance and, consequently, a greater value.

A very large proportion of the light incident on an effect pigment is reflected but a relatively small portion thereof is absorbed. Applying thin layers to the flat pigment core gives rise to interference phenomena, the intensity and spectrum of the reflected ray varying according to the angle of incidence and the viewing angle.

Starting from that principle, many effect pigments have already been proposed, none of which, however, is capable of meeting high requirements to the desired degree. Besides high gloss, optimum dichroism, a high degree of fastness to light and to weathering, compatibility with all application media, acceptability to the skin and in food, ease of handling and other requirements of users, production that is cheap, simple and exactly reproducible in terms of colour characteristics is also desirable.

U.S. Pat. No. 5,766,335 discloses effect pigments wherein a coating of a silicon oxide of composition $SiO_{0.25}$ to $SiO_{0.95}$ is applied to a transparent or metallically reflecting core. Optionally, further coatings of silicon dioxide or titanium dioxide are applied.

EP 0 874 026 A2 proposes coloured effect pigments that have a continuously variable composition. For example, such a coating consists of silicon and titanium oxides.

WO 00/18978 describes the production of gloss pigments in the form of plane-parallel flakes by vapour-deposition onto water- or alcohol-soluble inorganic compounds.

WO 00/43565 describes the vapour-deposition of a silicon monoxide layer that is oxidised to $SiO_2$ by tempering in air at from 150 to 500° C.

WO 01/57287 describes the production of gloss pigments by means of vapour-deposition, for example using silicon oxide as carrier layer and titanium oxide as metal oxide layer.

The invention relates to a pigment the particles of which have a length of from 2 μm to 5 mm, a width of from 2 μm to 2 mm and a thickness of from 50 nm to 1.5 μm and a ratio of length to thickness of at least 2:1, the particles having a core $S^D$ having two substantially parallel faces, the distance between which is the shortest axis of the core, and optionally having layers $Q^Z$ and/or $D^M$ applied to those parallel faces or to the entire surface, and wherein the core $S^D$ has a thickness of from 20 to 350 nm and comprises from 50 to 97 atom % silicon, bonded to from 3 to 95 atom % oxygen per 100 atom % silicon;

optionally, a layer $Q^Z$ having a thickness of from 0 to 500 nm is present, which is applied to the core $S^D$ and comprises from 17 to 51 atom % silicon, which is bonded to more than 95 atom % oxygen per 100 atom % silicon; and optionally, a layer $D^M$ having a thickness of from 0 to 300 nm is present, which has a transparency of from 50 to 100% and a complex refractive index $\tilde{N}=n+ik$ according to the condition $\sqrt{n^2+k^2} \geq 1.5$ at the wavelength of maximum visible reflection of the particles, which is substantially composed of carbon, an organic compound, a metal, a dielectric or a mixture thereof, and which is either on the core $S^D$ or, if a layer $Q^Z$ is present, is separated from the core $S^D$ by the layer $Q^Z$.

Unless otherwise specified, atom % refers to the totality of all atoms. The number of atom % of oxygen bonded to silicon per 100 atom % of silicon expresses the average stoichiometry of the silicon oxide in the core $S^D$ or in the layer $Q^Z$, with any impurities being disregarded even when they themselves also comprise oxygen (such as, for example, in $Fe_2O_3$). In the case of a chemical composition or stoichiometry that is variable over the thickness, 95 atom % of oxygen per 100 atom % of silicon is to be considered as the boundary between the core $S^D$ and the layer $Q^Z$. The composition of the core $S^D$ and of the layers $Q^Z$ and $D^M$ over the thickness can be determined, for example, by ESCA (electron spectroscopy for chemical analysis). Visible light is of wavelength from 400 to 700 nm. The complex refractive index $\tilde{N}$ (CRC Handbook of Chemistry and Physics, 82$^{nd}$ Edition, pages 12-133) can be determined, for example, by ellipsometry (R. M. A. Azzam & N. M. Bashera, *Ellipsometry and Polarized Light*, North Holland, New Amsterdam 1997).

The layers $Q^Z$ and/or $D^M$ are preferably arranged symmetrically about the core $S^D$, both with respect to their chemical composition and stoichiometry and to their thicknesses, having a plane of symmetry perpendicular to the thickness axis through the centre of the particles.

In addition to the optional layers $Q^Z$ and/or $D^M$, any desired further layers may also be present, although the production costs frequently are undesirably increased as a result. In high-value applications, for example automotive finishes, it is possible, for example, for the weathering resistance to be increased by means of an additional protective layer, from 2 to 250 nm thick (preferably from 10 to 100 nm thick), of an inorganic dielectric of $n_D \leq 1.6$ (such as $SiO_2$, $SiO(OH)_2$ etc.).

The pigments according to the invention comprise particles preferably having at least one layer $D^M$ or $Q^Z$, especially having at least one layer $D^M$, and more especially having both a layer $D^M$ and a layer $Q^Z$. Very special preference is accordingly given to particles having the layer sequences $Q^Z$-$S^D$-$Q^Z$ and $D^M$-$Q^Z$-$S^D$-$Q^Z$-$D^M$.

Figure 2:
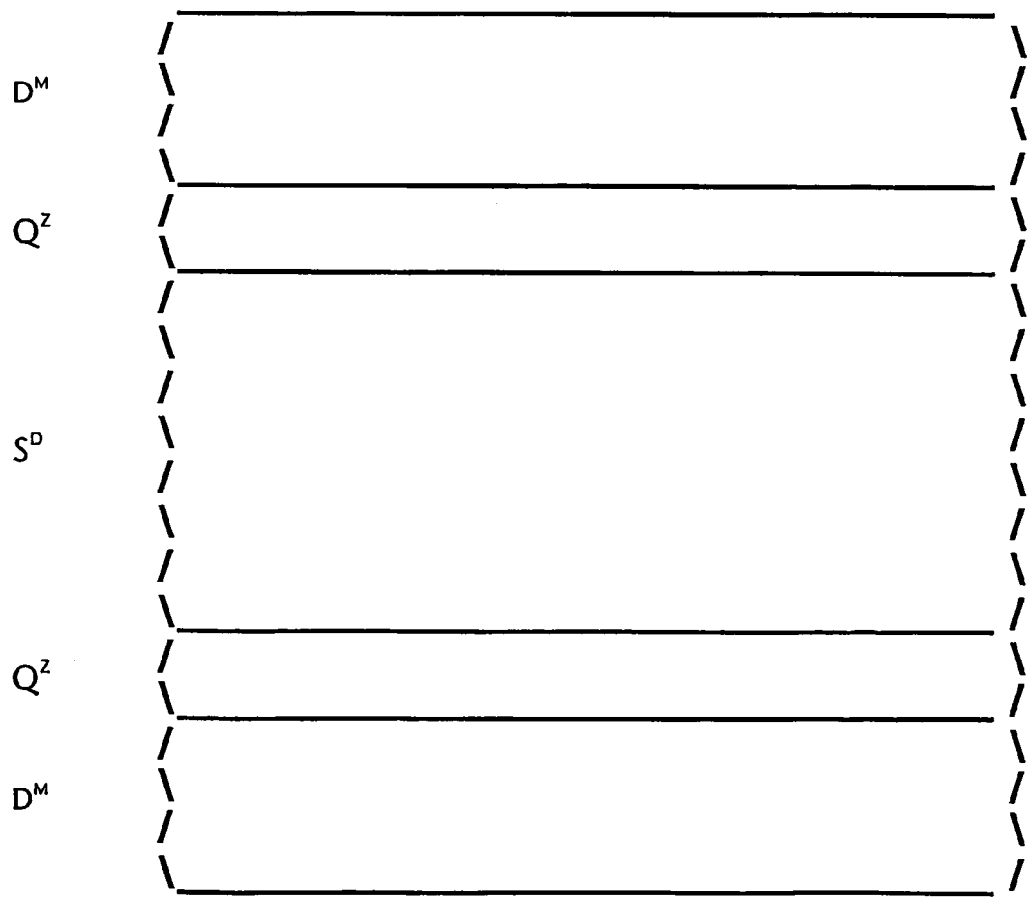

FIG. 1 is a section along the thickness axis of particles $Q^Z$-$S^D$-$Q^Z$. FIG. 2 is a section along the thickness axis of particles $D^M$-$Q^Z$-$S^D$-$Q^Z$-$D^M$.

The pigment particles preferably have lengths and widths of from 5 to 20 μm and a thickness of from 60 nm to 1.0 μm. The core SD comprises preferably from 60 to 93 atom % silicon, especially from 65 to 91 atom % silicon. The silicon in the core is bonded to preferably from 5 to 50 atom % oxygen, especially from 10 to 30 atom % oxygen, per 100 atom % silicon.

The layer $Q^Z$ has a thickness of preferably from 20 to 250 nm and comprises preferably from 20 to 40 atom % silicon, which is bonded to more than 150 atom % oxygen per 100 atom % silicon, especially from 30 to 36 atom % silicon, which is bonded to more than 178 atom % oxygen per 100 atom % silicon. Very especially the layer $Q^Z$ consists of at least 90 mol % $SiO_2$. The layer $D^M$ has a thickness of preferably from 20 to 200 nm, especially from 30 to 100 nm.

The layers $Q^Z$ and $D^M$ need not be present but offer advantages, both on an individual basis and in combination, with respect to colour characteristics and stability. Optionally, further layers may be applied thereto. The layer $D^M$ offers useful practical advantages especially when it is applied as the final layer in the vapour-deposition process or is formed immediately after vapour-deposition. Further layers may then be applied using relatively simple, for example chemical, methods.

It is also possible, however, to produce particles having the layer sequence $D^M$-$S^D$-$D^M$. Useful materials for the layer DM are, for example, metals such as Ag, Al, Au, Cu, Co, Cr, Fe, Ge, Mo, Nb, Ni, Si, Ti, V, alloys thereof, inorganic or organic pigments or colorants, graphite and compounds similar to graphite as disclosed in EP 0 982 376, $MoS_2$, metal oxides such as $TiO_2$, $ZrO_2$, SiO, $SiO_2$, $SnO_2$, $GeO_2$, ZnO, $Al_2O_3$, $V_2O_5$ $Fe_2O_3$, $Cr_2O_3$, $PbTiO_3$ or CuO, and mixtures thereof. The layer $D^M$ may, however, also consist of, for example, any of the many dielectric materials, likewise very well known to the person skilled in the art, whose specific electrical resistance is, according to the conventional definition, at least $10^{10}$ $\Omega \cdot cm$.

Preference is given to $TiO_2$ or mixtures of $TiO_2$ with other metal oxides, $TiO_2$ being especially in the rutile phase. The rutile phase of $TiO_2$ can be obtained, for example, in a manner known per se, for example by calcination of $TiO_2$ at about from 700 to 1000° C. in the presence of $SnO_2$ in an amount of customarily from 1 to 5% by weight, based on $TiO_2$.

The transparency of the layer $D^M$ is advantageously at least 50%, corresponding to a reflectivity of at most 50%. Using a metal, the skilled person will know how to achieve this by means of appropriately thin layers, for example using up to about 3 nm of Al or Au or up to about 10 nm of Co or Cu. In the case of colourless or coloured dielectrics greater thicknesses are possible.

Silicon oxides having a less-than-equimolar oxygen content ($SiO_x$ wherein $0.03 \leq x \leq 0.95$, especially $0.05 \leq x \leq 0.5$, more especially $0.1 \leq x \leq 0.3$) have astonishingly high stability to oxidation whilst having a high refractive index, even in thin layers. Hydrolysis or heating in the presence of oxygen at from 150 to 500° C., preferably from 200 to 300° C., unexpectedly results solely in a superficial silicon dioxide layer that is very thin, for example about 20 nm thick, which represents a very convenient method of producing structures having the layer sequence $Q^Z$-$S^D$-$Q^Z$. If thicker silicon dioxide layers are desired, they can be conveniently produced analogously to the method of the second implementation example of WO-00/43565 by means of vapour-deposition of silicon monoxide and subsequent tempering. It is advantageous therein that the layer of silicon oxide lying underneath the silicon dioxide and having a less-than-equimolar oxygen content remains unchanged.

Further layers may subsequently be applied to structures having the layer sequence $Q^Z$-$S^D$-$Q^Z$, for example in order to obtain $D^M$-$Q^Z$-$S^D$-$Q^Z$-$D^M$, which may be produced especially conveniently by wet-chemical application of a layer $D^M$ onto structures having the layer sequence $Q^Z$-$S^D$-$Q^Z$.

The core $S^D$ is produced, for example, by vapour-deposition onto a medium that can be readily dissolved away subsequently, as disclosed, for example, in DE 19 844 357, EP 0 990 715, U.S. Pat. No. 5,135,812, U.S. Pat. No. 6,270,840, WO 93/08237, WO 00/18978, WO 01/57287 or any of the references cited therein. For vapour-depositing the core $S^D$ there is advantageously used metallic silicon, which need not be of high purity. On the contrary, it is preferable to use silicon having a content of less than 99.999% by weight Si, for example from 50 to 99.9% by weight Si, especially from 60 to 99% by weight Si, more especially from 90 to 99% by weight Si, very especially from 95 to 98.5% by weight Si. Impurities may be present, for example elements of the main groups 13, 14 and 15 and/or transition elements such as Fe, Al, Ge, Sn and/or Sb.

The layers $Q^Z$ or $D^M$ may be produced, for example, by vapour-deposition in like manner, in which case—for symmetrical structures—vapour-deposition commences with the layer $D^M$ or $Q^Z$, onto which the core and then a further layer $Q^Z$ or $D^M$ are vapour-deposited. When layers $Q^Z$ and $D^M$ are both desired, the procedure is, for example, as described hereinbefore.

The particles of the pigment according to the invention can, where appropriate, be integrated into a polymer, for example obtainable by emulsion polymerisation as known per se in many variants for toner particles, or by incorporation into a thermoplastic or into a polymer dispersion or solution.

The pigments according to the invention can be used for all customary purposes, for example for colouring polymers in the mass, surface coatings (including effect finishes, including those for the automotive sector) and printing inks, and also, for example, for applications in cosmetics. Such applications are known from reference works, for example "Industrielle Organische Pigmente" (W. Herbst+K. Hunger, VCH Weinheim/New York, new editions continually published in German and English).

It has, however, been found that pigments according to the invention are of such outstanding quality that they can frequently be considered for applications in which hitherto obtainable effect pigments have not been entirely satisfactory. The skilled person is expressly recommended to carry out appropriate tests in this regard.

The pigments according to the invention are goniochromatic and result in brilliant, highly saturated (lustrous) colours. Especially advantageous colour characteristics are possessed by effect pigments having their main reflectivity at $\geq 600$ nm, which appear a highly saturated red in perpendicular view and yellow in flat view. The colour characteristics thereof are not achieved by effect pigments known hitherto.

The pigments according to the invention are accordingly very especially suitable for combination with conventional, transparent pigments, for example organic pigments such as, for example, diketopyrrolopyrroles, quinacridones, dioxazines, perylenes, isoindolinones etc., it being possible for the transparent pigment to have a similar colour to the effect pigment. Especially interesting combination effects are obtained, however, in analogy to, for example, EP 388 932 or EP 402 943, when the colour of the transparent pigment and that of the effect pigment are complementary.

The pigments according to the invention can be used with excellent results for pigmenting high molecular weight organic material.

The high molecular weight organic material for the pigmenting of which the pigments or pigment compositions according to the invention may be used may be of natural or synthetic origin. High molecular weight organic materials usually have molecular weights of about from $10^3$ to $10^8$ g/mol or even more. They may be, for example, natural resins, drying oils, rubber or casein, or natural substances derived therefrom, such as chlorinated rubber, oil-modified alkyd resins, viscose, cellulose ethers or esters, such as ethylcellulose, cellulose acetate, cellulose propionate, cellulose acetobutyrate or nitrocellulose, but especially totally synthetic organic polymers (thermosetting plastics and thermoplastics), as are obtained by polymerisation, polycondensation or polyaddition. From the class of the polymerisation resins there may be mentioned, especially, polyolefins, such as polyethylene, polypropylene or polyisobutylene, and also substituted polyolefins, such as polymerisation products of vinyl chloride, vinyl acetate, styrene, acrylonitrile, acrylic acid esters, methacrylic acid esters or butadiene, and also copolymerisation products of the said monomers, such as especially ABS or EVA.

From the series of the polyaddition resins and polycondensation resins there may be mentioned condensation products of formaldehyde with phenols, so-called phenoplasts, and condensation products of formaldehyde with urea, thiourea or melamine, so-called aminoplasts, and the polyesters used as surface-coating resins, either saturated, such as alkyd resins, or unsaturated, such as maleate resins; also linear polyesters and polyamides, polyurethanes or silicones.

The said high molecular weight compounds may be present singly or in mixtures, in the form of plastic masses or melts. They may also be present in the form of their monomers or in the polymerised state in dissolved form as film-formers or binders for surface coatings or printing inks, such as, for example, boiled linseed oil, nitrocellulose, alkyd resins, melamine resins and urea-formaldehyde resins or acrylic resins.

Depending on the intended purpose, it has proved advantageous to use the effect pigments or effect pigment compositions according to the invention as toners or in the form of preparations. Depending on the conditioning method or intended application, it may be advantageous to add certain amounts of texture-improving agents to the effect pigment before or after the conditioning process, provided that this has no adverse effect on use of the effect pigments for colouring high molecular weight organic materials, especially polyethylene. Suitable agents are, especially, fatty acids containing at least 18 carbon atoms, for example stearic or behenic acid, or amides or metal salts thereof, especially magnesium salts, and also plasticisers, waxes, resin acids, such as abietic acid, rosin soap, alkylphenols or aliphatic alcohols, such as stearyl alcohol, or aliphatic 1,2-dihydroxy compounds containing from 8 to 22 carbon atoms, such as 1,2-dodecanediol, and also modified colophonium maleate resins or fumaric acid colophonium resins. The texture-improving agents are added in amounts of preferably from 0.1 to 30% by weight, especially from 2 to 15% by weight, based on the end product.

The effect pigments according to the invention can be added in any tinctorially effective amount to the high molecular weight organic material being pigmented. A pigmented composition comprising a high molecular weight organic material and from 0.01 to 80% by weight, preferably from 0.1 to 30% by weight, based on the high molecular weight organic material, of a pigment according to the invention is advantageous. Concentrations of from 1 to 20% by weight, especially of about 10% by weight, can often be used in practice.

High concentrations, for example those above 30% by weight, are usually in the form of concentrates ("masterbatches") which can be used as colorants for producing pigmented materials having a relatively low pigment content, the pigments according to the invention having an extraordinarily low viscosity in customary formulations so that they can still be processed well.

For the purpose of pigmenting organic materials, the effect pigments according to the invention may be used singly. It is, however, also possible, in order to achieve different hues or colour effects, to add any desired amounts of other colour-imparting constituents, such as white, coloured, black or effect pigments, to the high molecular weight organic substances in addition to the effect pigments according to the invention. When coloured pigments are used in admixture with the effect pigments according to the invention, the total amount is preferably from 0.1 to 10% by weight, based on the high molecular weight organic material. Especially high goniochromicity is provided by the preferred combination of an effect pigment according to the invention with a coloured pigment of another colour, especially of a complementary colour, with colorations made using the effect pigment and colorations made using the coloured pigment having, at a measurement angle of 10°, a difference in hue ($\Delta H^*$) of from 20 to 340, especially from 150 to 210.

Preferably, the effect pigments according to the invention are combined with transparent coloured pigments, it being possible for the transparent coloured pigments to be present either in the same medium as the effect pigments according to the invention or in a neighbouring medium. An example of an arrangement in which the effect pigment and the coloured pigment are advantageously present in neighbouring media is a multi-layer effect surface coating.

The pigmenting of high molecular weight organic substances with the pigments according to the invention is carried out, for example, by admixing such a pigment, where appropriate in the form of a masterbatch, with the substrates using roll mills or mixing or grinding apparatuses. The pigmented material is then brought into the desired final form using methods known per se, such as calendering, compression moulding, extrusion, coating, pouring or injection moulding. Any additives customary in the plastics industry, such as plasticisers, fillers or stabilisers, can be added to the polymer, in customary amounts, before or after incorporation of the pigment. In particular, in order to produce non-rigid shaped articles or to reduce their brittleness, it is desirable to add plasticisers, for example esters of phosphoric acid, phthalic acid or sebacic acid, to the high molecular weight compounds prior to shaping.

For pigmenting surface coatings and printing inks, the high molecular weight organic materials and the effect pigments according to the invention, where appropriate together with customary additives such as, for example, fillers, other pigments, siccatives or plasticisers, are finely dispersed or dissolved in the same organic solvent or solvent mixture, it being possible for the individual components to be dissolved or dispersed separately or for a number of components to be dissolved or dispersed together, and only thereafter for all the components to be brought together.

Dispersing an effect pigment according to the invention in the high molecular weight organic material being pigmented, and processing a pigment composition according to the invention, are preferably carried out subject to conditions under which only relatively weak shear forces occur so that the effect pigment is not broken up into smaller portions. The permissible shear force corresponds approximately to that which is suitable for gentle dispersion of a mica of similar dimensions in a high molecular weight organic material and with which the skilled person will generally be well acquainted.

The colorations obtained, for example in plastics, surface coatings or printing inks, especially in surface coatings or printing inks, more especially in surface coatings, are distinguished by excellent properties, especially by extremely high saturation, outstanding fastness properties and high goniochromicity.

When the high molecular weight material being pigmented is a surface coating, it is especially a speciality surface coating, very especially an automotive finish.

The pigments according to the invention are also suitable for making-up the lips or the skin and for colouring the hair or the nails.

The invention accordingly relates also to a cosmetic preparation or formulation comprising from 0.0001 to 90% by weight of a pigment according to the invention and from 10 to 99.9999% of a cosmetically suitable carrier material, based on the total weight of the cosmetic preparation or formulation.

Such cosmetic preparations or formulations are, for example, lipsticks, blushers, foundations, nail varnishes and hair shampoos.

The pigments may be used singly or in the form of mixtures. It is, in addition, possible to use pigments according to the invention together with other pigments and/or colorants, for example in combinations as described hereinbefore or as known in cosmetic preparations.

The cosmetic preparations and formulations according to the invention preferably contain the pigment according to the invention in an amount from 0.005 to 50% by weight, based on the total weight of the preparation.

Suitable carrier materials for the cosmetic preparations and formulations according to the invention include the customary materials used in such compositions.

The cosmetic preparations and formulations according to the invention may be in the form of, for example, sticks, ointments, creams, emulsions, suspensions, dispersions, powders or solutions. They are, for example, lipsticks, mascara preparations, blushers, eye-shadows, foundations, eyeliners, powder or nail varnishes.

If the preparations are in the form of sticks, for example lipsticks, eye-shadows, blushers or foundations, the preparations consist for a considerable part of fatty components, which may consist of one or more waxes, for example ozokerite, lanolin, lanolin alcohol, hydrogenated lanolin, acetylated lanolin, lanolin wax, beeswax, candelilla wax, microcrystalline wax, carnauba wax, cetyl alcohol, stearyl alcohol, cocoa butter, lanolin fatty acids, petrolatum, petroleum jelly, mono-, di- or tri-glycerides or fatty esters thereof that are solid at 25° C., silicone waxes, such as methyloctadecane-oxypolysiloxane and poly(dimethylsiloxy)stearoxysiloxane, stearic acid monoethanolamine, colophane and derivatives thereof, such as glycol abietates and glycerol abietates, hydrogenated oils that are solid at 25° C., sugar glycerides and oleates, myristates, lanolates, stearates and dihydroxystearates of calcium, magnesium, zirconium and aluminium.

The fatty component may also consist of a mixture of at least one wax and at least one oil, in which case the following oils, for example, are suitable: paraffin oil, purcelline oil, perhydrosqualene, sweet almond oil, avocado oil, calophyllum oil, castor oil, sesame oil, jojoba oil, mineral oils having a boiling point about from 310 to 410° C., silicone oils, such as dimethylpolysiloxane, linoleyl alcohol, linolenyl alcohol, oleyl alcohol, cereal grain oils, such as wheatgerm oil, isopropyl lanolate, isopropyl palmitate, isopropyl myristate, butyl myristate, cetyl myristate, hexadecyl stearate, butyl stearate, decyl oleate, acetyl glycerides, octanoates and decanoates of alcohols and polyalcohols, for example of glycol and glycerol, ricinoleates of alcohols and polyalcohols, for example of cetyl alcohol, isostearyl alcohol, isocetyl lanolate, isopropyl adipate, hexyl laurate and octyl dodecanol.

The fatty components in such preparations in the form of sticks may generally constitute up to 99.91% by weight of the total weight of the preparation.

The cosmetic preparations and formulations according to the invention may additionally comprise further constituents, such as, for example, glycols, polyethylene glycols, polypropylene glycols, monoalkanolamides, non-coloured polymeric, inorganic or organic fillers, preservatives, UV filters or other adjuvants and additives customary in cosmetics.

They comprise, for example, a natural or synthetic or partially synthetic di- or tri-glyceride, a mineral oil, a silicone oil, a wax, a fatty alcohol, a Guerbet alcohol or an ester thereof, a lipophilic functional cosmetic active ingredient, including sun-protection filters, or a mixture of such substances.

A lipophilic functional cosmetic active ingredient suitable for skin cosmetics, an active ingredient composition or an active ingredient extract is an ingredient or a mixture of ingredients that is approved for dermal or topical application. The following may be mentioned by way of example:

active ingredients having a cleansing action on the skin surface and the hair; these include all substances that serve to cleanse the skin, such as oils, soaps, synthetic detergents and solid substances;

active ingredients having a deodorising and perspiration-inhibiting action: they include antiperspirants based on aluminium salts or zinc salts, deodorants comprising bactericidal or bacteriostatic deodorising substances, for example triclosan, hexachlorophene, alcohols and cationic substances, such as, for example, quaternary ammonium salts, and odour absorbers, for example ®Grillocin (combination of zinc ricinoleate and various additives) or triethyl citrate (optionally in combination with an antioxidant, such as, for example, butyl hydroxytoluene) or ion-exchange resins;

active ingredients that offer protection against sunlight (UV filters): suitable active ingredients are filter substances (sunscreens) that are able to absorb UV radiation from sunlight and convert it into heat; depending on the desired action, the following light-protection agents are preferred: light-protection agents that selectively absorb sunburn-causing high-energy UV radiation in the range of approximately from 280 to 315 nm (UV-B absorbers) and transmit the longer-wavelength range of, for example, from 315 to 400 nm (UV-A range), as well as light-protection agents that absorb only the longer-wavelength radiation of the UV-A range of from 315 to 400 nm (UV-A absorbers);

suitable light-protection agents are, for example, organic UV absorbers from the class of the p-aminobenzoic acid derivatives, salicylic acid derivatives, benzophenone derivatives, dibenzoylmethane derivatives, diphenyl acrylate derivatives, benzofuran derivatives, polymeric UV absorbers comprising one or more organosilicon radicals, cinnamic acid derivatives, camphor derivatives, trianilino-s-triazine derivatives, phenylbenzimidazolesulfonic acid and salts thereof, menthyl anthranilates, benzotriazole derivatives, and/or an inorganic micropigment selected from aluminium oxide- or silicon dioxide-coated $TiO_2$, zinc oxide or mica.

active ingredients against insects (repellents) are agents that are intended to prevent insects from touching the skin and becoming active there; they drive insects away and evaporate slowly; the most frequently used repellent is diethyl toluamide (DEET); other common repellents will be found, for example, in "Pflegekosmetik" (W. Raab and U. Kindl, Gustav-Fischer-Verlag Stuttgart/New York, 1991) on page 161.

active ingredients for protection against chemical and mechanical influences: these include all substances that form a barrier between the skin and external harmful substances, such as, for example, paraffin oils, silicone oils, vegetable oils, PCL products and lanolin for protection against aqueous solutions, film-forming agents, such as sodium alginate, triethanolamine alginate, polyacrylates, polyvinyl alcohol or cellulose ethers for protection against the effect of organic solvents, or substances based on mineral oils, vegetable oils or silicone oils as "lubricants" for protection against severe mechanical stresses on the skin;

moisturising substances: the following substances, for example, are used as moisture-controlling agents (moisturisers): sodium lactate, urea, alcohols, sorbitol, glycerol, propylene glycol, collagen, elastin and hyaluronic acid;

active ingredients having a keratoplastic effect: benzoyl peroxide, retinoic acid, colloidal sulfur and resorcinol;

antimicrobial agents, such as, for example, triclosan or quaternary ammonium compounds;

oily or oil-soluble vitamins or vitamin derivatives that can be applied dermally: for example vitamin A (retinol in the form of the free acid or derivatives thereof), panthenol, pantothenic acid, folic acid, and combinations thereof, vitamin E (tocopherol), vitamin F; essential fatty acids; or niacinamide (nicotinic acid amide);

vitamin-based placenta extracts: active ingredient compositions comprising especially vitamins A, C, E, $B_1$, $B_2$, $B_6$, $B_{12}$, folic acid and biotin, amino acids and enzymes as well as compounds of the trace elements magnesium, silicon, phosphorus, calcium, manganese, iron or copper;

skin repair complexes: obtainable from inactivated and disintegrated cultures of bacteria of the bifidus group;

plants and plant extracts: for example arnica, aloe, beard lichen, ivy, stinging nettle, ginseng, henna, camomile, marigold, rosemary, sage, horsetail or thyme;

animal extracts: for example royal jelly, propolis, proteins or thymus extracts;

cosmetic oils that can be applied dermally: neutral oils of the Miglyol 812 type, apricot kernel oil, avocado oil, babassu oil, cottonseed oil, borage oil, thistle oil, groundnut oil, gamma-oryzanol, rosehip-seed oil, hemp oil, hazelnut oil, blackcurrant-seed oil, jojoba oil, cherry-stone oil, salmon oil, linseed oil, cornseed oil, macadamia nut oil, almond oil, evening primrose oil, mink oil, olive oil, pecan nut oil, peach kernel oil, pistachio nut oil, rape oil, rice-seed oil, castor oil, safflower oil, sesame oil, soybean oil, sunflower oil, tea tree oil, grapeseed oil or wheatgerm oil.

The preparations in stick form are preferably anhydrous but may in certain cases comprise a certain amount of water which, however, in general does not exceed 40% by weight, based on the total weight of the cosmetic preparation.

If the cosmetic preparations and formulations according to the invention are in the form of semi-solid products, that is to say in the form of ointments or creams, they may likewise be anhydrous or aqueous. Such preparations and formulations are, for example, mascaras, eyeliners, foundations, blushers, eye-shadows, or compositions for treating rings under the eyes.

If, on the other hand, such ointments or creams are aqueous, they are especially emulsions of the water-in-oil type or of the oil-in-water type that comprise, apart from the pigment, from 1 to 98.8% by weight of the fatty phase, from 1 to 98.8% by weight of the aqueous phase and from 0.2 to 30% by weight of an emulsifier.

Such ointments and creams may also comprise further conventional additives, such as, for example, fragrances, antioxidants, preservatives, gel-forming agents, UV filters, colorants, pigments, pearlescent agents, non-coloured polymers as well as inorganic or organic fillers.

If the preparations are in the form of a powder, they consist substantially of a mineral or inorganic or organic filler such as, for example, talcum, kaolin, starch, polyethylene powder or polyamide powder, as well as adjuvants such as binders, colorants etc.

Such preparations may likewise comprise various adjuvants conventionally employed in cosmetics, such as fragrances, antioxidants, preservatives etc.

If the cosmetic preparations and formulations according to the invention are nail varnishes, they consist essentially of nitrocellulose and a natural or synthetic polymer in the form of a solution in a solvent system, it being possible for the solution to comprise other adjuvants, for example pearlescent agents.

In that embodiment, the coloured polymer is present in an amount of approximately from 0.1 to 5% by weight.

The cosmetic preparations and formulations according to the invention may also be used for colouring the hair, in which case they are used in the form of shampoos, creams or gels that are composed of the base substances conventionally employed in the cosmetics industry and a pigment according to the invention.

The cosmetic preparations and formulations according to the invention are prepared in conventional manner, for example by mixing or stirring the components together, optionally with heating so that the mixtures melt.

The Examples that follow illustrate the invention without limiting the scope thereof (unless otherwise indicated, "%" is always % by weight):

EXAMPLE 1

One graphite crucible containing silicon granules (purity: 98.3% by weight Si, 0.72% by weight Fe, 0.6% by weight Al, traces O) and one containing sodium chloride are placed as materials to be vapour-deposited in a vacuum vapour-deposition chamber having a rotating aluminium drum as the target. At a pressure of about 0.1 Pa, 100 nm of sodium chloride are first vapour-deposited and then, in the course of 100 seconds, 100 nm of silicon in the form of a low-oxide compound (by reaction with some of the oxygen that is present). The coated aluminium drum is immersed in water; the product, which breaks up into particles, is recovered by filtration, rinsed with water and dried in air at 150° C. A brilliant green power having a goniochromatic effect is obtained.

EXAMPLE 2

The procedure is analogous to Example 1, but 120 nm of silicon in the form of a low-oxide compound are vapour-deposited. A brilliant orange-red powder having a goniochromatic effect is obtained.

EXAMPLE 3

The procedure is analogous to Example 1, but 125 nm of silicon in the form of a low-oxide compound are vapour-deposited. A brilliant red powder having a goniochromatic effect is obtained.

EXAMPLE 4

The procedure is analogous to Example 1, but 130 nm of silicon in the form of a low-oxide compound are vapour-deposited. A brilliant purple powder having a goniochromatic effect is obtained.

EXAMPLE 5

The procedure is analogous to Example 1, but 100 nm of sodium chloride are first vapour-deposited and then 25 nm of silicon monoxide, 90 nm of silicon in the form of a low-oxide compound and again 25 nm of silicon monoxide. Heating is subsequently carried out in air at 250° C. for 1 hour, whereupon the outer layer is converted into silicon dioxide, at the same time increasing in thickness. A brilliant purple powder having a strong goniochromatic effect is obtained.

EXAMPLE 6

The procedure is analogous to Example 5, but 100 nm of sodium chloride are first vapour-deposited and then 50 nm of $TiO_2$, 25 nm of silicon dioxide, 100 nm of silicon in the form of a low-oxide compound, 25 nm of silicon dioxide and 50 nm of $TiO_2$. A brilliant blue-green powder having a strong goniochromatic effect is obtained.

EXAMPLE 7

The procedure is analogous to Example 5, but 100 nm of sodium chloride are first vapour-deposited and then 50 nm of $TiO_2$, 25 nm of silicon dioxide, 50 nm of silicon in the form of a low-oxide compound, 25 nm of silicon dioxide and 50 nm of $TiO_2$. A violet powder having a strong goniochromatic effect is obtained. The marked difference in colour saturation between 30° and 60° is especially noteworthy.

EXAMPLE 8

The procedure is analogous to Example 5, but 100 nm of sodium chloride are first vapour-deposited and then 50 nm of $TiO_2$, 50 nm of silicon dioxide, 50 nm of silicon in the form of a low-oxide compound, 50 nm of silicon dioxide and 50 nm of $TiO_2$. A blue powder having high colour saturation and a strong goniochromatic effect is obtained. The fact that a maximum in respect of colour saturation is achieved at about 30° is noteworthy.

EXAMPLE 9

The procedure is analogous to Example 5, but 100 nm of sodium chloride are first vapour-deposited and then 50 nm of $TiO_2$, 100 nm of silicon dioxide, 50 nm of silicon in the form of a low-oxide compound, 100 nm of silicon dioxide and 50 nm of $TiO_2$. A yellow-green powder having a strong goniochromatic effect is obtained. The marked difference in hue between 30° and 60° is especially noteworthy.

EXAMPLE 10

The procedure is analogous to Example 5, but 100 nm of sodium chloride posited and then 100 nm of $TiO_2$, 100 nm of silicon dioxide, 100 nm of silicon in the form of a low-oxide compound, 100 nm of silicon dioxide and 100 nm of $TiO_2$. A red-violet powder is obtained.

EXAMPLE 11

The procedure is analogous to Example 5, but 100 nm of sodium chloride are first vapour-deposited and then 100 nm of $TiO_2$, 50 nm of silicon dioxide, 100 nm of silicon in the form of a low-oxide compound, 50 nm of silicon dioxide and 100 nm of $TiO_2$. An orange powder is obtained.

EXAMPLE 12

The procedure is analogous to Example 5, but 100 nm of sodium chloride are first vapour-deposited and then 100 nm of $TiO_2$, 25 nm of silicon dioxide, 100 nm of silicon in the form of a low-oxide compound, 25 nm of silicon dioxide and 100 nm of $TiO_2$. A yellow powder is obtained.

EXAMPLE 13

A lipstick base has the following composition:

| Number | Substance | Amount [%] |
| --- | --- | --- |
| 1 | cera alba | 11.4 |
| 2 | candelilla wax | 8.1 |
| 3 | carnauba wax | 3.8 |
| 4 | Lunacera M | 6.0 |
| 5 | castor oil | 38.8 |
| 6 | Controx KS | 0.1 |
| 7 | aroma oil | 1.0 |
| 8 | Amerlate P | 2.5 |
| 9 | OH lan | 1.6 |
| 10 | isopropyl palmitate | 10.1 |
| 11 | Dow Corning 556 | 2.8 |
| 12 | Dow Corning 1401 | 3.3 |
| 13 | $TiO_2$ pigment | 2.3 |
| 14 | pigment according to Example 4 | 8.2 |
| | Total | 100.0 |

Substances 8-10 are mixed together, and substances 13 and 14 are dispersed in the resulting mixture. The resulting paste is then passed several times through a three-roll apparatus. In the meantime, substances 1-6 are melted, stirred together until homogeneous, and then substances 7, 11 and 12 are stirred in. The two mixtures are then mixed together in the hot state until homogeneous distribution is achieved. The hot mass is then poured into a lipstick mould and allowed to cool. The resultings lipsticks have an intense blue-tinged red colour of outstanding light fastness and very good gloss and exhibit no bleeding.

EXAMPLES 14-25

Figure 3:
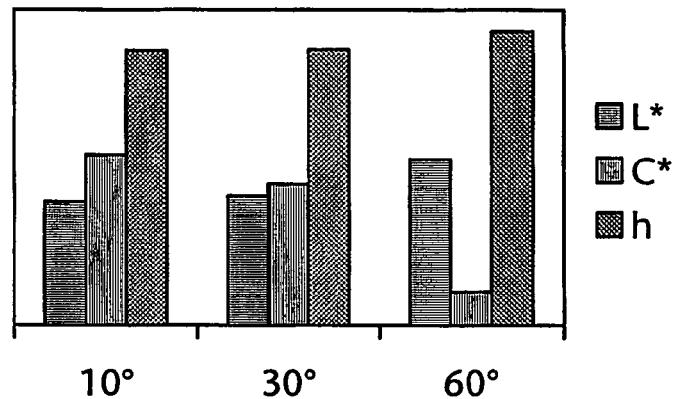
Figure 4:
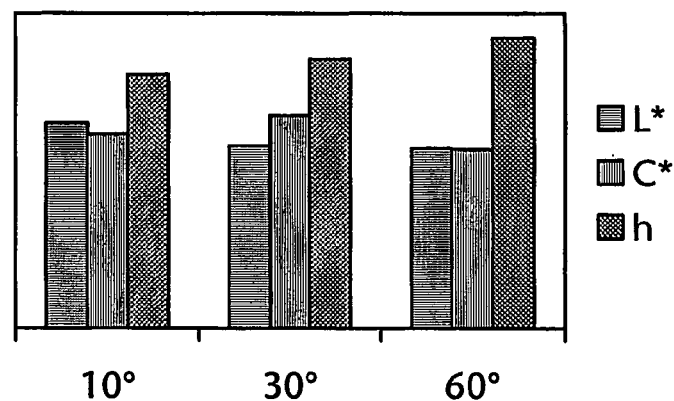
Figure 5:
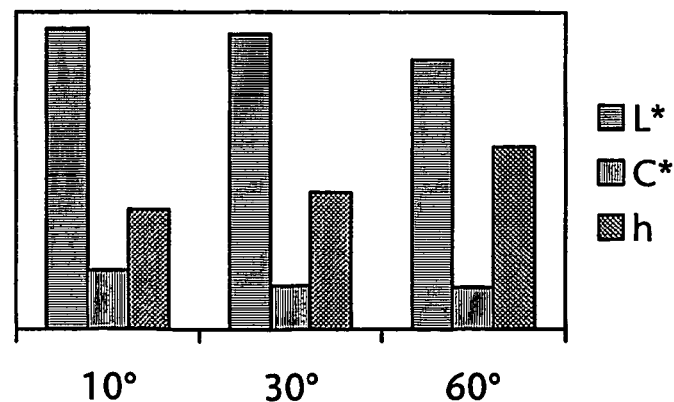

For the purpose of measuring the goniochromatic effect, Examples 1-12 are repeated but, instead of sodium chloride being vapour-deposited, vapour-deposition is carried out onto glass. The coated glass plates are placed against a black background and measured by means of a goniophotospectrometer (e.g. from Zeiss) with $D_{65}$ illumination at the viewing angles 10°, 30° and 60°, using the C.I.E. 64 conversion. FIGS. 3 to 5 give the C.I.E. 1976 L*C*h colour coordinates as a function of the angle, the Y axis being scaled from 0 to 100 for L* and C* and from 0 to 360 for h. FIG. 3 corresponds to coating onto glass analogous to Example 7, FIG. 4 to coating onto glass analogous to Example 8, and FIG. 5 to coating onto glass analogous to Example 9.

EXAMPLES 26-37

100 parts by weight of a formulation comprising 7.8 parts by weight of a pigment according to one of Examples 1-12, 45.4 parts by weight Alkydal® F 310 (Bayer, 60% in Solventnaphtha™ 100), 4 parts by weight Disperbyk® 161 (Byk Chemie, 30% in n-butyl acetate/1-methoxy-2-propyl acetate 1:6), 0.8 part by weight of silicone oil 1% in xylene, 3.3 parts by weight 1-methoxy-2-propanol, 3.3 parts by weight n-butanol, 15.4 parts by weight xylene, 19.4 parts by weight Maprenal® MF 650 (Solutia Inc., 30% in isobutanol/1-butanol/xylene 40:2:2 max.) and 0.6 part by weight Tinuvin® 123 are dispersed using 230 parts by weight of glass beads in a dispersing machine for 2 hours at about 40° C. After separating off the glass beads, the relevant layer thicknesses of the surface coating are sprayed onto black-primed aluminium sheets, the amount applied per sheet being about 10, 20, 30 or 40 g/m². The surface coatings are then allowed to vaporise for 30 minutes at about 25° C. and then stoved for 30 minutes at 130° C. The reflection of D65 illumination perpendicular to the surface is measured at angles of 10°, 20°, 30°, 40°, 50°, 60°, 70° and 80° to the surface (C.I.E. 1976 L*C*h colour coordinates). All the surface coatings are goniochromatic.

What is claimed is:

1. A pigment the particles of which have a length of from 2 μm to 5 mm, a width of from 2 μm to 2 mm and a thickness of from 50 nm to 1.5 μm and a ratio of length to thickness of at least 2:1, the particles having a core $S^D$ having two substantially parallel faces, the distance between which is the shortest axis of the core, and optionally having layers $Q^Z$ and/or $D^M$ applied to those parallel faces or to the entire surface, and wherein the core $S^D$ has a thickness of from 20 to 350 nm and comprises from 50 to 97 atom % silicon, bonded to from 3 to 95 atom % oxygen per 100 atom % silicon;

optionally, a layer $Q^Z$ having a thickness of from 0 to 500 nm is present, which is applied to the core $S^D$ and comprises from 17 to 51 atom % silicon, which is bonded to more than 95 atom % oxygen per 100 atom % silicon; and optionally, a layer $D^M$ having a thickness of from 0 to 300 nm is present, which has a transparency of from 50 to 100% and a complex refractive index $\tilde{N}=n+ik$ according to the condition $\sqrt{n^2+k^2} \geq 1.5$ at the wavelength of maximum visible reflection of the particles, which is substantially composed of carbon, an organic compound, a metal, a dielectric or a mixture thereof, and which is either on the core $S^D$ or, in the presence of a layer $Q^Z$, is separated from the core $S^D$ by the layer $Q^Z$.

2. A pigment according to claim 1, additionally surrounded by an additional layer, from 2 to 250 nm thick, of an inorganic dielectric of $n_D \leq 1.6$.

3. A pigment according to claim 2, wherein the dielectric of the additional layer is a silicon oxide that may optionally be partly or completely hydrolysed.

4. A pigment according to claim 1, which, in a surface coating having a pigment concentration of 15% by weight, based on the surface coating, has, on measurement of the reflection under D65 illumination, a hue angle h of from 350 to 30 at a measurement angle of 80° to the surface of the surface coating and a hue angle h of from 70 to 120 at a measurement angle of 30° to the surface of the surface coating.

5. A composition, comprising a high molecular weight organic material and from 0.01 to 80% by weight, based on the high molecular weight organic material, of a pigment according to claim 1.

6. A composition according to claim 5, wherein the high molecular weight organic material is a surface coating.

7. A surface coating wherein measurement of the reflection under D65 illumination results in a hue angle h of from 350 to 30 at a measurement angle of 80° to the surface and in a hue angle h of from 70 to 120 at a measurement angle of 30° to the surface.

8. A cosmetic preparation or formulation comprising from 0.0001 to 90% by weight of a pigment according to claim 1, and from 10 to 99.9999% of a cosmetically suitable carrier material, based on the total weight of the cosmetic preparation or formulation.

9. A pigment according to claim 1, additionally surrounded by an additional layer, from 10 to 100 nm thick, of an inorganic dielectric of $n_D \leq 1.6$.

10. A composition, comprising a high molecular weight organic material and from 0.1 to 30% by weight, based on the high molecular weight organic material, of a pigment according to claim 1.

* * * * *